United States Patent
Craig et al.

(10) Patent No.: US 6,214,927 B1
(45) Date of Patent: Apr. 10, 2001

(54) METHOD FOR MAKING AQUEOUS EMULSIONS OF FUNCTIONALIZED ORGANOPOLYSILOXANES

(75) Inventors: Daniel Horace Craig, Niskayuna; Wayne Francis Morgan, Mechanicville, both of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/432,001

(22) Filed: Nov. 2, 1999

(51) Int. Cl.[7] ............... C08K 9/10; C08G 77/08; C08G 77/382
(52) U.S. Cl. ............... 524/837; 525/477; 525/902; 424/70.12
(58) Field of Search ............... 516/58, 66; 524/837; 525/477, 902; 424/70.12

(56) References Cited

U.S. PATENT DOCUMENTS

| | | | |
|---|---|---|---|
| 2,891,920 | * 6/1959 | Hyde et al. | 524/837 |
| 3,294,725 | 12/1966 | Findlay et al. | 524/837 |
| 4,859,740 | * 8/1989 | Damrath et al. | 525/902 |
| 4,861,831 | * 8/1989 | Damrath et al. | 525/902 |
| 4,935,464 | * 6/1990 | Ona et al. | 524/837 |
| 5,223,586 | * 6/1993 | Mautner et al. | 525/477 |
| 5,726,270 | 3/1998 | Craig | 524/837 |
| 5,776,454 | * 7/1998 | Gee et al. | 424/70.12 |
| 5,856,402 | 1/1999 | Craig et al. | 524/837 |
| 5,900,460 | 5/1999 | Craig | 524/837 |

FOREIGN PATENT DOCUMENTS 0 459 500 A2 * 12/1991 (EP).

* cited by examiner

Primary Examiner—Robert Dawson
Assistant Examiner—Daniel S. Metzmaier
(74) Attorney, Agent, or Firm—B M Bennett; N C Johnson

(57) ABSTRACT

A method is provided for making aqueous emulsions of functionalized organopolysiloxane particles having a volume average particle diameter in a range between about 300 nanometers to about 1 micron. The aqueous silicone emulsions can be employed as part of a coating composition, for example, a shampoo, to impart improved surface characteristics.

19 Claims, No Drawings

METHOD FOR MAKING AQUEOUS EMULSIONS OF FUNCTIONALIZED ORGANOPOLYSILOXANES

BACKGROUND OF THE INVENTION

The present invention is directed to a method of making stable aqueous emulsions of organopolysiloxane particles having a volume average particle diameter (Dv) of at least about 300 nanometers (nm) which have been functionalized with a chemically combined polar group such as a mercaptoorgano, epoxyorgano, or carboxy group.

There is shown by Craig in U.S. Pat. Nos. 5,726,270, 5,856,402, and 5,900,460, semi-continuous methods for making acid catalyzed aqueous dispersions of organopolysiloxane particles from cyclic poly(diorganosiloxane)s. The aqueous dispersions of organopolysiloxane particles have been found to be useful in coating applications including personal care. For example, in the formulation of a silicone composition useful in hair shampoos, experience has shown that desirable results can be achieved with the use of an aqueous dispersion of organopolysiloxane particles having a volume average particle diameter in the range between about 300 nanometers and about 1 micron. It has been found that improvements in hair styling can be obtained with a silicone-containing shampoo, because the silicone can impart a "smoothing out" effect. It is speculated that shampoos containing silicones in the form of aqueous dispersions of organopolysiloxane particles having a volume average particle diameter (Dv) of at least about 300 nanometers, can more readily coat the surface of the hair shaft to achieve a smoother surface.

It also has been suggested that additional enhancements can be obtained in coating and personal care applications based on the use of aqueous dispersions of organopolysiloxane particles by modifying the dispersed particles with a polar functional group, such as a mercaptoorgano, epoxyorgano, or carboxy radical. However, previous efforts to synthesize aqueous emulsions of functionalized organopolysiloxane particles having a volume average particle diameter of at least about 300 nanometers in a semi-continuous manner have been unsuccessful. Attempts to incorporate an organosilicon polar functionalizing source material, for example an alkoxy silane having a polar functional group attached to silicon by a carbon-silicon bond, into an aqueous organopolysiloxane equilibration mixture of cyclic poly(diorganosiloxane) using a conventional acid catalyst typically results in organopolysiloxane particles with volume average particle diameter less than 300 nanometers. It is speculated that the limitation in particle size growth in such a polar group-substituted alkoxysilane-containing mixture is due to a difference in reactivity between the cyclic poly(diorganosiloxane) and alkoxysilane in an acid catalyzed environment. A satisfactory method is therefor needed to make stable aqueous emulsions of functionalized organopolysiloxane particles having a volume average particle diameter of at least about 300 nanometers using an acid catalyzed process.

BRIEF SUMMARY OF THE INVENTION

In one embodiment, the present invention is a method for making a substantially stable aqueous emulsion having a total solids content in a range between about 5% and about 60% by weight of functionalized organopolysiloxane particles, comprising effecting reaction at a temperature in a range between about 25° C. and about 110° C., and in the presence of an effective amount of an acid catalyst surfactant, between (A) an aqueous emulsion of organopolysiloxane particles consisting essentially of chemically combined diorganosiloxy units and having a volume average particle diameter of at least about 300 nanometers, and (B) an organosilicon polar functionalizing source material, wherein there is utilized in the resulting reaction mixture by weight in a range between about 0.1 and about 20 parts of (B) per 100 parts of (A).

In another embodiment, the present invention is a method for making a substantially stable aqueous emulsion having a solids content in a range between about 5% and about 60% by weight of functionalized organopolysiloxane particles having a volume average particle diameter of at least about 300 nanometers, comprising the steps of:

(1) equilibrating a cyclic poly(diorganosiloxane) in a semi-continuous manner in the presence of an effective amount of an acid catalyst surfactant to form an aqueous emulsion of organopolysiloxane particles having a volume average particle diameter of at least about 300 nanometers, and (2) effecting reaction between the organopolysiloxane particles in the aqueous emulsion of (1), and an organosilicon polar functionalizing source material in a range between about 0.1 part and about 20 parts by weight per 100 parts of such organopolysiloxane particles.

DETAILED DESCRIPTION OF THE INVENTION

As used hereinafter, the term "organosilicon polar functionalizing source material" means a polar group-substituted alkoxy silane, cyclic poly(diorganosiloxane), or poly(diorganosiloxane) fluid, said fluid having a viscosity which can include a range between about 10 centipoise and about $10^5$ centipoise at 25° C., depending upon the particular chemically combined functional group, such as a mercaptoorgano, epoxyorgano, or carboxy group, or a mixture thereof. The term "substantially stable aqueous emulsion" means an emulsion in which the dispersed particles do not appreciably agglomerate during the typical shelf-life of the emulsion. "Semi-continuous" in one of its embodiments refers to a process for functionalizing organopolysiloxane particles which employs organopolysiloxane particle seeds prepared in a separate step. In other embodiments, "semi-continuous" refers to a reaction which does not need to be stopped in order to add more reactants.

The present invention is based on the discovery that an average particle size of organopolysiloxane particles can be substantially maintained during functionalization of such particles by reducing or avoiding direct contact between the organosilicon polar functionalizing source material and the organopolysiloxane precursor, for example an appropriate cyclic poly(diorganosiloxane). "Substantially maintained" refers to a volume average particle size of organopolysiloxane particles which changes less than about 50%, preferably less than about 20%, and most preferably less than about 10%. Accordingly, useful results have been achieved by effecting direct contact under suitable equilibration conditions and in the presence of an acid catalyst surfactant, between the organosilicon polar functionalizing source material and an aqueous emulsion of organopolysiloxane particles, or "seeds" having a volume average particle diameter of at least about 300 nanometers.

In one embodiment, a substantially stable aqueous emulsion of functionalized organopolysiloxane particles with the desired size range is produced by a two-staged, acid-catalyzed semi-continuous/semi-continuous or semi-continuous/batch process whereby the particle size is substantially maintained from the first stage and functionalization occurs in a second stage through equilibration of a polar group-substituted alkoxy silane, cyclic poly(diorganosiloxane), or poly(diorganosiloxane) fluid into the particles. Often, a semi-continuous process is utilized in the first stage wherein, for example, a cyclic poly(diorganosiloxane), acid catalyst surfactant, and water are added to a preheated reactor, either as separate feeds or in various combinations with each other, or as a pre-emulsified mixture containing water and optionally additional surfactant over some specified time period. The reaction mixture may be heated for a period of time after addition of precursor to ensure formation of organopolysiloxane particles in the desired size range. Upon completion of the first stage, the reaction mixture may be cooled to any desired temperature, for example to about room temperature, or maintained at reaction temperature. The organosilicon polar functionalizing source material may be added, either semi-continuously or batchwise, at which point the reactor may be heated to a desired reaction temperature or simply maintained at a desired reaction temperature for a period of time to ensure equilibration of functionalized species into the particles. The length of time between stages may be of any convenient duration provided a particle size in the desired range is substantially achieved in the first stage and adequate functionality incorporation is achieved in the second stage.

In another embodiment, a substantially stable aqueous emulsion of functionalized organopolysiloxane particles with the desired size range is produced by post-functionalization of a pre-existing, pre-synthesized organopolysiloxane emulsion comprising particles with volume average particle diameter of at least about 300 nanometers. Post-functionalization using organosilicon polar functionalizing source material may be performed essentially as described above. The synthesis of the pre-existing emulsion can occur at any point prior to the functionalization step, including a separate emulsion manufacturing step.

Aqueous emulsions of organopolysiloxane particles used in the practice of the present invention can be employed as preformed organopolysiloxane particles or "seeds". Said particles typically have a volume average particle diameter (Dv) of at least about 300 nm, and preferably in the range of from about 300 nm to about 1 micron. Alternatively, the initial volume average particle diameter of said particles may be less than about 300 nanometers and is increased to greater than about 300 nanometers before functionalization, for example through equilibration with cyclic poly(diorganosiloxane) in the presence of a catalyst.

Another source of organopolysiloxane particles used in the practice of the present invention is by equilibrating at least one cyclic poly(diorganosiloxane) under semi-continuous conditions. Accordingly, an aqueous mixture having in a range between about 5% and about 60% by weight of cyclic poly(diorganosiloxane) can be agitated and equilibrated in the presence of an acid catalyst surfactant at temperatures in the range between about 25° C. and about 110° C. Equilibration of the cyclic poly(diorganosiloxane) can be conducted in a semi-continuous manner to form poly(diorganosiloxane) particles having a volume average particle diameter of greater than about 300 nanometers, and preferably in the range between about 300 nanometers and about 1 micron.

Cyclic poly(diorganosiloxane)s included in the practice of the invention, are for example, one or more members selected from a $C_{3-8}$ cyclic diorganosiloxane, and most preferably a $C_{3-4}$ cyclic poly(dimethylsiloxane), such as hexamethyltrisiloxane and octamethylcyclotetrasiloxane, or "tetramer". However, other $C_{1-6}$ organo radicals can be present in addition to or in place of methyl, such as ethyl, propyl, butyl and phenyl.

Acid catalyst surfactants include, for example, surface-active sulfonic acids, which can be substituted with alkyl, alkaryl, or aryl radicals. Examples of mixtures of surface-active sulfonic acid salts with strong mineral acids, and combinations thereof are disclosed in U.S. Pat. No. 3,294,725, also can be used. A particularly preferred acid catalyst surfactant is dodecylbenzenesulfonic acid. An effective amount of the acid catalyst surfactant is in a range between about 0.25% and about 5% by weight of acid catalyst surfactant based on the weight of cyclic poly(diorganosiloxane) initially present in the aqueous mixture. Preferred weight ratios of cyclic poly(diorganosiloxane) to acid catalyst surfactant to water can vary in a range between about 70:1:29 and about 75:5:20.

Among the organosilicon polar functionalizing source materials there are included alkoxy silanes having the formula, $$(RO)_a(Z)_b Si$$

where R is a $C_{1-6}$ alkyl radical, for example, methyl, ethyl, propyl, and butyl, Z is a polar group selected from the group consisting of mercaptoorgano, epoxyorgano, and carboxy, or a mixture thereof, "a" is an integer equal to 1 to 3 inclusive, "b" is an integer equal to 1 to 3 inclusive, and the sum of a and b is 4. Some of the mercaptoorgano groups in useful mercaptoorganoalkoxysilanes are, for example, mercaptoalkyls, such as mercaptopropyl, mercaptobutyl and mercaptophenylethylene.

Certain poly(diorganosiloxane) fluids having chemically combined functional groups as previously shown, also can be used as organosilicon polar functionalizing source materials. These poly(diorganosiloxane) fluids preferably have viscosities in the range between about 10 centipoise and about $10^5$ centipoise at 25° C. There are included within the poly(diorganosiloxane) fluids $C_{3-8}$ cyclic poly(diorganosiloxane)s, for example, hexaorgano, and tetraorgano cyclic poly(diorganosiloxane)s, having at least one chemically combined polar group, and the balance of substituents being $C_{1-6}$ organo radicals, for example, alkyl, aryl, such as phenyl, and preferably methyl. In addition, the poly(diorganosiloxane) fluids can be linear having a viscosity in a range between about 10 and about $10^5$ centipoise at 25° C. The poly(diorganosiloxane) fluids can have in a range between about 5 mole percent and about 100 mole percent of diorganosiloxy units having at least one chemically combined polar group as previously identified, based on the total moles of chemically combined diorganosiloxy units, such as dimethylsiloxy units. Additional information about suitable poly(diorganosiloxane) fluids can be found in Silicones, Hardman and Torkelson, Encyclopedia of Chemical Technology, Volume 15, pp. 205–308, John Wiley & Sons.

Reaction between organopolysiloxane particles and organosilicon polar functionalizing source materials can be effected at temperatures in a range between about 25° C. and about 110° C. Depending upon such factors as the identity of the source material, it may be preferred to add the organosilicon polar functionalizing source material to existing organopolysiloxane particles at temperatures in a range between about room temperature and about 90° C. and preferably at temperatures in a range between about room temperature and about 40° C. to minimize premature hydrolysis of alkoxysilicon groups which may result in unwanted coagulum (heterogeneous polysiloxane product) and lower product yield. The final product emulsion typically has in a range between about 5% by weight and about 60% by weight and preferably in a range between about 30% by weight and about 55% by weight solids level.

In order that those skilled in the art will be better able to practice the present invention, the following examples are given by way of illustration, and not by way of limitation. In these examples, all parts which are referenced are by weight unless otherwise indicated.

EXAMPLE 1

A reactor contained 450 grams of water which was continuously stirred and was at a temperature of 86° C. A pre-emulsified mixture of 300 grams of water, 9.2 grams of dodecylbenzenesulfonic acid, and 927 grams of octamethylcyclotetrasiloxane was added to the reactor over 405 minutes. There was then added batchwise to the reactor 6.2 grams of gamma-mercaptopropyltrimethoxysilane. The reaction mixture was then maintained at 86° C. for an additional 4 hours and allowed to cool to room temperature.

Based on method of preparation and a Nicomp 370 Submicron Particle Sizer instrument applying a Gaussian analysis protocol, there was obtained an emulsion of mercapto-functionalized poly(dimethylsiloxane) particles having a volume average particle diameter (Dv) of 659 nanometers. A solids content of 51.1 weight percent and a small amount of coagulum was also found utilizing a CEM Labwave 9000 gravimetric microwave drier with 20 minute heat times at full microwave output.

CONTROL EXAMPLE 1

In an analogous run to Example 1, a pre-emulsified mixture of 100 grams of water, 3.3 grams of dodecylbenzenesulfonic acid, 329.5 grams of octamethylcyclotetrasiloxane, and 1.9 grams gamma-mercaptopropyltrimethoxysilane was added with stirring over 355 minutes to a reactor containing 150 grams of water at 86° C. There was added an additional 200 grams of water to lower reaction mixture viscosity. The resulting mixture was maintained for an additional 4 hours at 86° C., then cooled to room temperature. Based on method of preparation, there was obtained an aqueous emulsion of mercapto-functionalized poly(dimethylsiloxane) particles. However, the volume average particle diameter of the mercapto-functionalized poly(dimethylsiloxane) particles was found to be 264 nanometers based on the use of a Nicomp 370 Submicron Particle Sizer instrument applying a Gaussian analysis protocol. The solids content of the mixture was found to be 39.2% by weight.

EXAMPLE 2

A reactor contained 450 grams of water which was continuously stirred and was at a temperature of 86° C. A pre-emulsified mixture of 300 grams of water, 9.5 grams of dodecylbenzenesulfonic acid, and 933 grams of octamethylcyclotetrasiloxane was added to the reactor over 405 minutes. The reaction mixture was heated an additional 8 hours and then cooled to room temperature. There was then added batchwise to the reactor 12.75 grams of gamma-mercaptopropyltrimethoxysilane, reheated to 86° C. and maintained at that temperature for an additional 12 hours, allowed to cool to room temperature, and characterized as in Example 1. There was obtained an emulsion of mercapto-functionalized poly(dimethylsiloxane) particles having a volume average particle diameter of 720 nanometers. A solids content of 52 weight percent and no coagulum was also found.

EXAMPLE 3

Over a period of 362 minutes there was added to a reactor having 450 grams of water at 86° C. which was being continuously stirred, a pre-emulsified mixture of 300 grams of water, 9.36 grams of dodecylbenzenesulfonic acid, 0.2 grams of tetramethyldivinyldisiloxane, and 936 grams of octamethylcyclotetrasiloxane. The resulting reaction mixture was heated for an additional 30 minutes and then cooled rapidly. Based on method of preparation and the use of a Nicomp 370 Submicron Particle Sizer instrument applying a Gaussian analysis protocol, and a CEM Labwave 9000 gravimetric microwave drier, there was obtained an aqueous emulsion having 51.3% solids by weight, and organopolysiloxane particles having a volume average particle diameter of 903 nanometers, and consisting essentially of chemically combined dimethylsiloxy units.

The above emulsion was treated at 34° C. with a batchwise addition of 27.2 grams of methyltrimethoxysilane. The resulting mixture was reheated to 86° C. and maintained at that temperature for 6 hours. The mixture was cooled to room temperature. The resulting emulsion was found to be free of coagulum. The Dv of the resulting alkoxy functionalized organopolysiloxane particles was found to be substantially unchanged. The aqueous silicone emulsion is useful for imparting improved surface characteristics in hair treatment.

EXAMPLE 4

A reactor having 450 grams of water was continuously stirred at a temperature of 86° C. Over a period of 367 minutes a pre-emulsified mixture of 300 grams of water, 9.5 grams of dodecylbenzenesulfonic acid, and 937 grams of octamethylcyclotetrasiloxane. The resulting reaction mixture was heated for an additional 30 minutes and then cooled rapidly. The above emulsion was treated at 32° C. with a batch-wise addition of a mixture of 9.6 grams gamma-mercaptopropyltrimethoxysilane and 17.9 grams of methyltrimethoxysilane. The resulting mixture was reheated to 86° C. and maintained at that temperature for 6 hours, then cooled to room temperature and characterized as in Example 1. There was obtained an aqueous emulsion having 51.1% solids by weight, and organopolysiloxane particles having a volume average particle diameter of 769 nanometers. The emulsion was found to be free of coagulum. The aqueous silicone emulsion is useful for imparting improved surface characteristics in hair treatment.

Although the above examples are directed to only a few illustrations of the advantages achieved in the practice of the method of the present invention, it should be understood that the method of the present invention can be used to make a much broader variety of silicone emulsions as set forth in the description preceding these examples.

What is claimed:

1. A method for making a substantially stable aqueous emulsion having a total solids content in a range between about 5% by weight and about 60% by weight of functionalized organopolysiloxane particles, comprising effecting reaction at a temperature in a range between about 25° C. and about 110° C., and in the presence of an effective amount of an acid catalyst surfactant, between (A) an aqueous emulsion of organopolysiloxane particles consisting essentially of chemically combined diorganosiloxy units and having a volume average particle diameter of at least about 300 nanometers, and (B) an organosilicon polar functionalizing source material comprising a mercaptoorgano group, an epoxy organo group, a carboxy group, or mixtures thereof, wherein there is utilized in the resulting reaction mixture in a range between about 0.1 part and about 20 parts by weight of (B) per 100 parts of (A); and wherein said volume average particle diameter is substantially maintained upon functionalization.

2. The method in accordance with claim 1, wherein the organopolysiloxane particles consist essentially of chemically combined dimethylsiloxy units.

3. The method in accordance with claim 1, wherein the organosilicon polar functionalizing source material comprises a mercaptoalkoxysilane.

4. The method in accordance with claim 1, wherein the acid catalyst surfactant comprises dodecylbenzenesulfonic acid.

5. A method for making a substantially stable aqueous emulsion according to claim 1 wherein the volume average particle diameter changes less than about 20% upon functionalization.

6. A method for making a substantially stable aqueous emulsion according to claim 1 wherein the volume average particle diameter changes less than about 10% upon functionalization.

7. A method for making a substantially stable aqueous emulsion having a total solids content in a range between about 30% by weight and about 55% by weight of functionalized organopolysiloxane particles, comprising effecting reaction at a temperature in the range between about room temperature and about 40° C., and in the presence of an effective amount of an acid catalyst surfactant, between (A) an aqueous emulsion of organopolysiloxane particles consisting essentially of chemically combined diorganosiloxy units and having a volume average particle diameter in a range between about 300 nanometers and about 1 micron, and (B) a mercaptoorganoalkoxysilane, wherein there is utilized in the resulting reaction mixture in a range between about 0.1 part and about 20 parts by weight of (B) per 100 parts of (A); and wherein said volume average particle diameter is substantially maintained upon functionalization.

8. A method for making a substantially stable aqueous emulsion according to claim 7 wherein the volume average particle diameter changes less than about 20% upon functionalization.

9. A method for making a substantially stable aqueous emulsion according to claim 7 wherein the volume average particle diameter changes less than about 10% upon functionalization.

10. A method for making a substantially stable aqueous emulsion having a total solids content in a range between about 5% by weight and about 60% by weight of functionalized organopolysiloxane particles having a volume average particle diameter of at least about 300 nanometers, comprising the steps of:

(1) equilibrating a cyclic poly(diorganosiloxane) in a semi-continuous manner in the presence of an effective amount of an acid catalyst surfactant to form an aqueous emulsion of organopolysiloxane particles having a volume average particle diameter of at least about 300 nanometers; and (2) effecting reaction between the organopolysiloxane particles in the aqueous emulsion of (1), and an organosilicon polar functionalizing source material comprising a mercaptoorgano group, an epoxy organo group, a carboxy group, or mixtures thereof, wherein the organosilicon polar functionalizing source material is present in a range between about 0.1 part and about 20 parts by weight per 100 parts of such organopolysiloxane particles; and wherein said volume average particle diameter is substantially maintained upon functionalization.

11. The method in accordance with claim 10, wherein the cyclic poly(diorganosiloxane) comprises octamethylcyclotetrasiloxane.

12. The method in accordance with claim 10, wherein the acid catalyst surfactant comprises dodecylbenzenesulfonic acid.

13. The method in accordance with claim 10, wherein the organosilicon polar functionalizing source material comprises a mercaptoalkoxysilane.

14. The method in accordance with claim 13, wherein the organosilicon polar functionalizing source material comprises gamma-mercaptopropyltrimethoxysilane.

15. A method for making a substantially stable aqueous emulsion according to claim 10 wherein the volume average particle diameter changes less than about 20% upon functionalization.

16. A method for making a substantially stable aqueous emulsion according to claim 10 wherein the volume average particle diameter changes less than about 10% upon functionalization.

17. A method for making a substantially stable aqueous emulsion having a total solids content in a range between about 30% by weight and about 55% by weight of functionalized organopolysiloxane particles having a volume average particle diameter in a range between about 300 nanometers and about 1 micron, comprising the steps of:

(1) equilibrating a cyclic poly(diorganosiloxane) in a semi-continuous manner in the presence of an effective amount of an acid catalyst surfactant to form an aqueous emulsion of organopolysiloxane particles having a volume average particle diameter in a range between about 300 nanometers and about 1 micron; and (2) effecting reaction between the organopolysiloxane particles in the aqueous emulsion of (1), and a mercaptoorganoalkoxysilane in a range between about 0.1 part and about 20 parts by weight per 100 parts of such organopolysiloxane particles; and wherein said volume average particle diameter is substantially maintained upon functionalization.

18. A method for making a substantially stable aqueous emulsion according to claim 17 wherein the volume average particle diameter changes less than about 20% upon functionalization.

19. A method for making a substantially stable aqueous emulsion according to claim 17 wherein the volume average particle diameter changes less than about 10% upon functionalization.

* * * * *